(12) United States Patent
Neumüller

(10) Patent No.: US 7,005,506 B2
(45) Date of Patent: Feb. 28, 2006

(54) METHOD FOR PREPARING AN ALBUMIN ISOLATE FROM A SUBSTANCE CONTAINING ALBUMIN

(76) Inventor: Waldemar Neumüller, Wilhelm-Baum-Weg 29, D-37077 Göttingen (DE)

(*) Notice: Subject to any disclaimer, the term of this patent is extended or adjusted under 35 U.S.C. 154(b) by 328 days.

(21) Appl. No.: 10/365,933

(22) Filed: Feb. 13, 2003

(65) Prior Publication Data

US 2003/0229206 A1    Dec. 11, 2003

Related U.S. Application Data

(63) Continuation-in-part of application No. 09/914,343, filed on Aug. 22, 2001, now abandoned.

(30) Foreign Application Priority Data

Feb. 23, 1999 (DE) ............................... 199 07 725

(51) Int. Cl.
C07K 14/76 (2006.01)
(52) U.S. Cl. ..................... 530/412; 530/362
(58) Field of Classification Search ............. 530/412, 530/350, 407, 362; 436/88
See application file for complete search history.

(56) References Cited

U.S. PATENT DOCUMENTS

| | | | | |
|---|---|---|---|---|
| 4,443,540 A | 4/1984 | Chervan et al. | ............... | 435/69 |
| 4,559,307 A | 12/1985 | Hopkins | .................... | 435/272 |
| 6,140,469 A | 10/2000 | Shen et al. | ................. | 530/370 |

FOREIGN PATENT DOCUMENTS

| | | |
|---|---|---|
| DE | 1 203 588 | 9/1963 |
| DE | 43 39 743 C1 | 8/1995 |
| DE | 44 29 787 C2 | 8/1996 |
| EP | 0 700 641 A2 | 8/1963 |
| EP | 0 700 641 A3 | 8/1963 |
| GB | 1107229 | 8/1966 |
| JP | 63227171 | 9/1988 |
| WO | WO 95/14394 | 6/1995 |

OTHER PUBLICATIONS

Tanaka, T. et al. (2001)-terminal portion acts as an initiator of the inactivation of pepsin at neutral pH. Protein Eng. vol. 14, pp. 669-674.*

Zeki Berk, "Technology Of Production Of Edible Flours and Protein Products From Soybeans," FAO Agricultural Services Bulletin No. 97, Food and Agriculture Organization of the United Nations Rome 1992, http://www.fao.org/docrep/t0532e/to532e07.htm.

Takuji Tanaka and Rickey Y. Yada, "N-terminal portion acts as an initiator of the inactivation of pepsin at neutral pH," Protein Engineering vol. 14 No. 9 pp. 669-674, 2001.

* cited by examiner

Primary Examiner—Jon Weber
Assistant Examiner—Samuel Wei Liu
(74) Attorney, Agent, or Firm—Thomas, Kayden, Horstemeyer and Risley, LLP

(57) ABSTRACT

For preparing an albumin isolate from a substance containing albumin, the substance is first ground to a flour. The flour is then suspended in an aqueous solution. The albumin is extracted from the flour into the solution by an at least two stage extraction process using at least one protease, at a pH greater than 8 and at a temperature between 30 and 60° C. In the first stage the flour is treated at a lower protease to albumin weight ratio, at a lower pH and at a higher temperature than in the second stage. After the first stage, a first upper flow and a fraction containing the flour are separated, and the albumin is precipitated from said upper flow. The fraction containing the flour is subjected to the second extraction stage. After that, a second upper flow is separated and fed back to the first stage.

22 Claims, 1 Drawing Sheet

METHOD FOR PREPARING AN ALBUMIN ISOLATE FROM A SUBSTANCE CONTAINING ALBUMIN

CLAIM OF PRIORITY

This application is a continuation-in-part of U.S. application, Ser. No. 09/914,343, filed on Aug. 22, 2001 (abandoned) entitled, "Method For Preparing An Albumin Isolate From A Substance Containing Albumin," of the same title, which is the National Phase of Patent Cooperation Treaty Patent Application having Ser. No. WO 00/49887 filed Feb. 23, 2000, which claims priority to German Patent Application No. DE 199 07 725.8, filed Feb. 23, 1999, all of which are entirely incorporated herein by reference.

FIELD OF THE INVENTION

The invention relates to albumin isolates, and more particularly, to methods for preparing an albumin isolate from a substance containing albumin.

BACKGROUND

Several methods are known to extract albumin from vegetable raw materials, an alkaline extraction of the albumin at a pH of between 7 and 9 and at a temperature of 40 to 50° C. being the basis of these methods. The extracted albumin is then purified by centrifugation and acidified with a mineral acid until the isoelectric point of the albumin is reached. The albumin precipitated at the isoelectric point is again concentrated and purified by means of centrifugation. In this way, yields of 70% as related to the albumin contained in the raw materials are possible. However, it is a serious drawback that only such raw materials may be used in which the albumin has a low level of denaturation. Especially in exploring the most important vegetable albumin isolate, i.e., soya albumin isolate, the limitation to so called "white flakes" as a raw material is an economic drawback. White flakes are only obtained by means of a special drying method for the remainders of soya oil production. Normally, the remainders are dried less carefully, and they are then present in a form of so called "toasted flakes" in which the albumin is strongly denatured.

From DE 12 03 588 it is known to enhance the alkaline extraction process in exploring albumins from an albumin containing substance by means of a pre-treatment of an aqueous suspension of the substance with hydrogen peroxide within the alkaline range and with proteolytic enzymes. To this end, the pH of the suspension of the albumin containing substance is at first raised, then hydrogen peroxide is added and the temperature is raised to initiate peroxidation. Then, the pH is adjusted to 4 to 9, and enzymes are added to the suspension, the activity minimum of which is within this pH-range. Afterwards, the suspension is stirred for two hours. Preferably, vegetable enzymes like bromelaine, ficine and papaine are used. After the enzymatic hydrolysis, the albumin is dissolved in that the pH is raised to 9 to 12. At the same time, high temperatures are applied from which it is known that they result in albumin damages particularly in combination with the high pH. The multiple change of the pH in this known method requires great efforts in large scale applications and results in a high consumption of alkali and acid followed by a strong formation of salt.

It is also known from DE 44 29 787 C2 to use proteolytic enzymes for enhancing the solubility of albumins. Here, the starting material is at first extracted with alcohol, only afterwards it is mechanically broken up and then further enzymatically broken up in the acid to neutral range. The extraction of attendant material to the albumin is effected by means of a countercurrent process. A treatment with hydrogen peroxide can take place after the extraction of the albumin in this known method, too. Due to the use of alcohol for the extraction, the method requires high efforts which are disadvantageous. The explosion danger of the suspension and the inactivation of the used enzymes by the presence of alcohol have to be permanently considered. In the known method, the proteolyses is per definition limited to a pH-range of <9.5, only the pH-range of <7.5 being concretely described in DE 44 29 787 C2. On the other hand it is known to those skilled in the art that the solubility of albumin is particularly great, if the pH is over 9. All in all, the efficiency of the known method as compared to the cost to be spent for its application is only low so that the prepared albumin isolates are not competitive.

A method according the preamble of claim 1 is known from DE 43 39 743 C1. This method does without the use of alcohol. For dissolving the protein, however, a pH of over 11.5, particularly of about 12.5, is needed which is associated with a high consumption of alkali and of acid for a later neutralization. Prior to the proteolysis, the albumin containing substance is treated with a protease at a pH>10.5. The pre-treatment requires a comparatively large amount of enzyme, which results in a drawback with regard to the production cost. The comparatively high salt content at the end of the albumin, extraction of this known method, which in praxis requires an additional washing step, is a further drawback.

A method for extraction of albumin from an albumin containing substance which operates with high amounts of enzyme is also know from JP 2 076 597 A. An alkaline protease is added to an alkaline suspension of the albumin containing substance, the pH of which is between 10 and 13, and incubated at a temperature of 30 to 50° C. for 1 to 20 hours. Afterwards, neutralization and filtration of the suspension takes place. These indeed dramatic conditions of the albumin extraction result in extended albumin damages. As a result, it is only possible to obtain hydrolysates for cosmetic applications by the known method. It is unsuitable, however, for the preparation of albumin isolates as food.

SUMMARY OF THE INVENTION

Embodiments of the present invention include methods for preparing an albumin isolate from a substance that contains albumin. Briefly described, one embodiment of such a method includes grinding the substance to a flour; suspending the flour in an aqueous solution; extracting the albumin from the flour into the solution using at least one countercurrent protease; precipitating the albumin from the solution using mineral acid; and neutralizing the precipitated albumin. In one embodiment, extracting the albumin from the flour into the solution includes subjecting the flour suspended in the aqueous solution to an at least two stage treatment with the at least one protease, with a pH greater than 8 and with heat of temperatures between 30 and 60° C. The flour is treated in the first stage with a lower concentration of the at least one protease in relation to the albumin weight, with a lower pH and with a higher temperature than in the second stage. At the end of the first stage, a first overflow is separated from a fraction containing the flour, from which overflow the albumin is precipitated. At the end of the second stage, a second overflow is separated from a fraction containing the flour, which overflow is fed back to the first stage.

BRIEF DESCRIPTION OF THE DRAWING

Many aspects of the invention can be better understood with reference to the following drawing.

DETAILED DESCRIPTION

Figure 1:
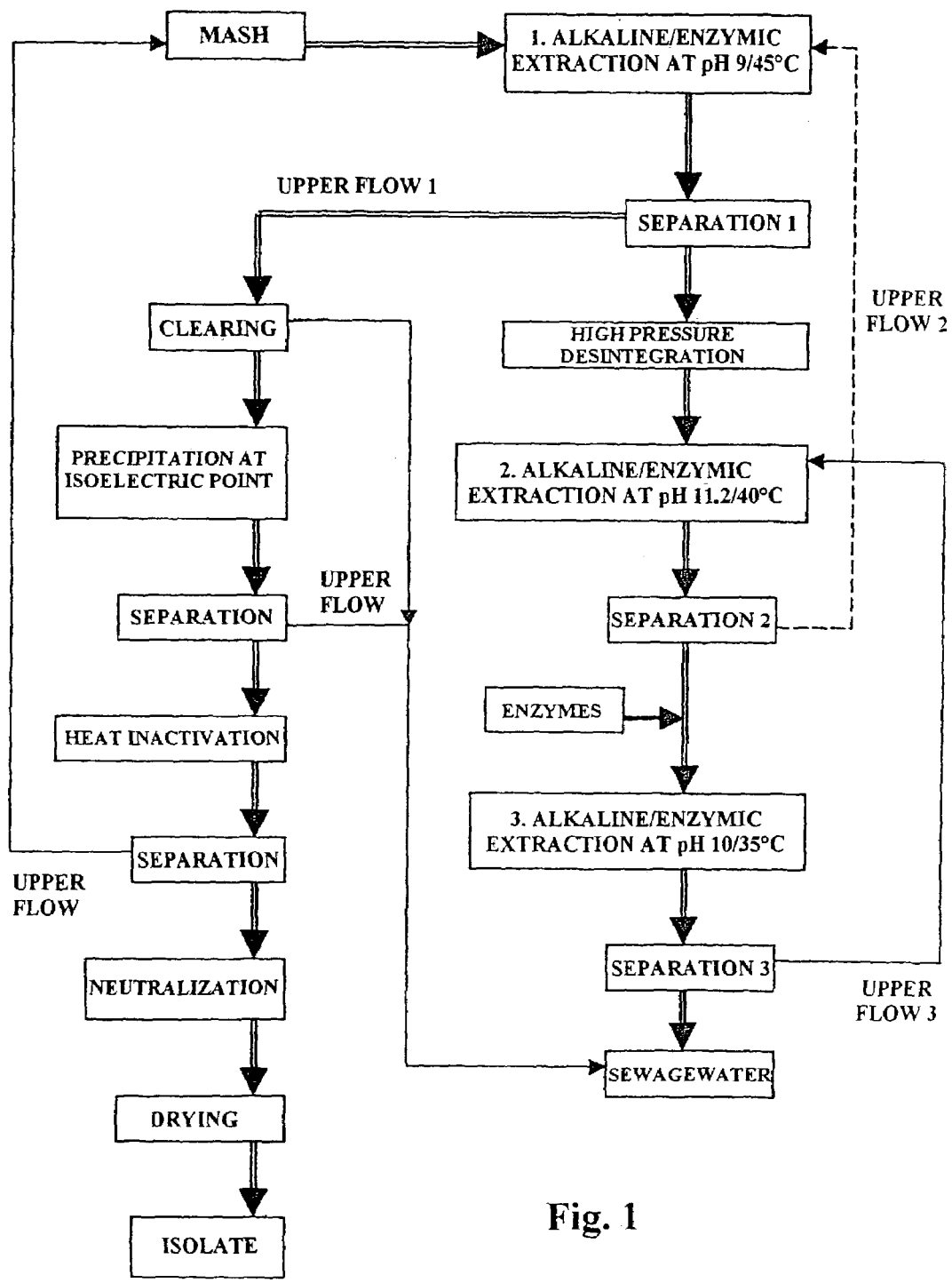
FIG. 1 shows a flow diagram of an embodiment of the method for preparing an albumin isolate from a substance that contains an albumin according to the invention.

Disclosed is a method for preparing an albumin isolate from a substance containing albumin which results in a better albumin yield while at the same time limiting use of agents such as water, alkali, acid and enzyme, all without reducing the quality of the prepared albumin isolate. The disclosed method can be used with albumin containing substances with both high and with low albumin solubility.

Embodiments of the invention include methods for preparing an albumin isolate from a substance that contains albumin. In this regard, one exemplary method includes: grinding the substance to a flour; suspending the flour in an aqueous solution; extracting the albumin from the flour into the solution using at least one countercurrent flow of protease; precipitating the albumin from the solution using mineral acid; and neutralizing the precipitated albumin. In one embodiment, extracting the albumin from the flour into the solution includes subjecting the flour suspended in the aqueous solution to an at least two stage treatment with the at least one protease, with a pH greater than 8 and with heat of temperatures that range from 30 to 60° C. The flour is treated in the first stage with a lower concentration of the at least one protease in relation to the albumin weight, with a lower pH and with a higher temperature than in the second stage. At the end of the first stage, a first overflow is separated from a fraction containing the flour, from which overflow the albumin is precipitated. At the end of the second stage, a second overflow is separated from a fraction containing the flour, which overflow is fed back to the first stage.

In a preferred embodiment, the mineral acid used to precipitate the albumin isolate from the solution may be selected from hydrochloric acid, sulfuric acid and/or phosphoric acid and combinations thereof. These particular mineral acids will not result in a chemical decomposition of the protein, if used according to the disclosed method, as the pH is preferably only lowered to the isoelectric point of the protein. Afterwards, the pH is raised again to neutralize the obtained albumin isolate.

Further, it is preferred that there are from at least two up to four extraction stages in the disclosed method. It is likely that more than four extraction steps would not be economic. Even more preferably, the flour suspended in the aqueous solution is subjected to a three-stage treatment. If the protease is only added during the last stage of the procedure, an increase in yield may not be achieved with further stages. In this situation, the three-stage treatment embodiment is especially preferred. In the three-stage treatment embodiment, it is preferred that the pH values in the three stages be greater than 8 and that the heat treatment temperatures range from about 30 to 60° C.

It is also preferred that the flour is treated in the third stage with a higher concentration of the at least one protease in relation to the albumin weight and with a lower temperature than in the second stage. A third overflow is separated from a fraction containing the flour after the third stage, which overflow is fed back into the second stage.

Further, it is preferred that the at least one protease used in the disclosed method is selected from at least one of the following: serine proteases, cysteine proteases, asparagine proteases, and metalloproteases. The specific proteases that could be used in the present invention are as follows, listed by their EC-numbers, which are the numbers assigned to the proteases by the Enzyme Commission (EC) of the International Union of Biochemistry (IUB), also referred to as IUB numbers: serine endopeptidases having EC numbers EC 3.4.21.XX, with XX being 1, 2, 4, 62, 63, 64, 65, 66, 80, 81, or 83; cysteine endopeptidases having EC numbers EC 3.4.22.XX, with XX being 2, 3, 4, 31, 32, or 33; aspartic endopeptidases having EC numbers EC 3.4.23.XX, with XX being 6 or 18; and/or metallo endopeptidases having EC numbers EC 3.4.24.XX, with XX being 4, 27, 28, 31, or 49; and combinations thereof. It should be noted that within the above listing some proteases may be mentioned twice because the EC-numbers of certain proteases have been changed in the past, e.g., EC 3.4.23.18 is now used to designate the same aspartic endopeptidase that was formerly designated as EC 3.4.23.6.

Some of the above-mentioned proteases are more preferred for being used in the invention than others. In particular, an industrial protease will preferably include more than one specific protease, i.e., it will be a protease mixture. Such a mixture preferably includes a combination of two or more of the above proteases.

Further, it is preferred that the at least one protease is inactivated in the albumin by means of a heat treatment.

In the new method, the dissolution of the albumins is effected out with the aid of an alkaline countercurrent extraction by means of a temperature gradient, different pH-values and a simultaneous application of albumin-cleaving enzymes during the extraction cascade. Within an individual case, this extraction can be supported by the application of hydrogen peroxide and/or alcohols.

With respect to pH, as noted above, it is preferred that the pH applied in the different stages of the invention be greater than 8. With a pH greater than 8, there is a useable dissolving effect on the albumin. With regard to a pH range for first and second stages of the disclosed method, preferably the pH range is approximately 8 to 10 for the first stage and approximately 8 to 11.5 for the second stage. Preferably, the pH in the second stage is higher than in the first stage. More preferably, the pH in the second stage is approximately 10.5 to 11.5. Thus, the maximum pH during the disclosed method is approximately 11.5.

Even though at the alkaline pH preferably present in the second stage not all proteases will show their maximum activity, there nevertheless is a remaining effective activity that may be used in the disclosed method. The effective activity of a protease will depend on its relative activity at the present pH, on its stability over time at the present pH, and on its relative activity at the present temperature. By way of example, even if the relative activity at pH 11 is only 50%, and the stability over the relevant period of time at pH 11 is only 50%, and the relative activity at the present temperature is only 50%, there is still an effective activity of the protease of 12.5% of its maximum activity. Thus, only very few proteases, which are very sensitive to high pH values, will not work in the disclosed method.

At the pH values present in the disclosed method, most proteases will not be fully destroyed by the alkalinity of the solution(s)/suspension(s). The effective activity of the protease used in the disclosed method is selected in order to both enhance the alkaline dissolution of the albumin and to produce an albumin isolate with certain properties. A higher effective activity of the protease will enhance the dissolution of the albumin in the albumin-containing substance and increase the solubility of the obtained albumin isolate.

In the disclosed method, the alkaline pH opens the folded albumins contained in the albumin-containing substance so that the protease can attack the albumins much easier than at lower pH levels. Facilitating attack of the albumins more than compensates for a reduced relative activity of the protease at the alkaline pH for most proteases. Thus, the positive effect of alkalinity on the reactivity of the albumins is outweighed by any potential negative effect on the reactivity of the protease(s). If a protease used in the disclosed method is particularly sensitive to alkaline pH values, then increasing the amount of protease used in the method may compensate for the decreased reactivity of the protease.

For example, a well suited alkaline protease will have an effective activity in the second stage of an embodiment of the disclosed method of at least about 20% of its maximum activity under optimum conditions. The reduction of the effective activity here is not due so much to the pH, but to the temperature present in the second stage, which is typically in the order of about 40° C. Thus, for example, an alkaline protease that has a relative activity of more than 90% at this pH, and which is stable at this pH over the relevant periods of time, will have an effective activity that normally will not exceed about 40% of the maximum activity of the protease under the instant method conditions. If, under the conditions of the second stage, the effective activity of a protease that is not an alkaline protease is, for example, only 10% of its maximum activity under optimum conditions, then the amount of the protease has to be doubled in order to achieve the same activity as with the alkaline protease having an effective activity of 20%. Thus, very high amounts of protease are used if the effective activity of the protease is very low under the given conditions.

Autolysis of the protease under these conditions typically does not begin until the weight ratio of enzyme to substrate is about 1:30. See John Shannon: "Using Proteinases for Edman Sequence Analysis and Peptide Mapping" (Rob Beynon and Judith S. Bond (eds.)) in *Proteolytic Enzymes*, Oxford University Press, 2001. In a preferred embodiment of the disclosed method, with the exemplary protease(s) the weight ratio of enzyme to albumin is about 1:100. This allows for addition of about three times more of a less suitable protease before approaching the ratio of about 1:30 where autolysis might begin. Additionally, autolysis of a protease is also dependent on the effective activity of the protease at the given pH and at the given temperature. Thus, if the effective activity of the protease is reduced by pH and temperature conditions, then the risk of autolysis of the protease is also reduced.

Only those proteases that have an effective activity under the conditions of the second that is smaller than about 0.5% of their maximum activity may be excluded from being used in the invention. Even a protease having an effective activity of about 0.5% could be raised in its activity to the activity level of a well suited alkaline protease in the second stage by using about 40 to 50 times more protease per weight of the albumin. For example, the disclosed method has been found to work with an acid protease like EC 3.4.23.18, with appropriate increased amounts of protease.

In the preferred method, the starting material, if it does not already have such a particle size, is milled into a flour with a particle size of about 30 to 100 microns ($\mu$m), and more preferably to a particle size of about 50 to 100 $\mu$m, and mixed with water at a ratio from about 1:5 to 1:8, and the suspension is raised to a temperature of about 30 to 60° C., particularly of about 50° C. Further, it is preferred that, before the step of extracting the albumin into the solution, the flour is subjected to a pre-treatment using at least one substance selected from the group comprising lyes, acids and enzymes.

The pH of the suspension is adjusted to 8 to 10, particularly to about 9, by means of alkaline or alkaline earth hydroxides. It is preferred that the albumin is extracted from the flour into the solution using at least one alcohol and/or hydrogen peroxide. To enhance the albumin solubility in this stage of extraction, a protease may be added at this point in the method. Preferably, however, only the cleared overflow or the filtrate of the following stage of extraction is added. The enzyme/albumin-ratio obtained should be from approximately 1 to 2,000 to 1 to 6,000. After an incubation time of about 10 to 60 min., particularly of about 20 min, a first separation takes place.

It is preferred that at least one of the overflows is separated from the fraction containing the flour in that the flour suspended in the solution is centrifuged on a decanter under vacuum. The use of a Sedikanter centrifuge obtained from Flottweg GmbH, Germany providing a force field of about 6,000×acceleration of gravity (g) for the separation is preferred. During the separation, a formation of foam may be essentially avoided by means of a vacuum surrounding. A suitable vacuum is in the range of an absolute pressure of about 300 to 500 mbar. In this way, processing of albumin suspensions without an antifoam agent is successful. If it is not possible to carry out the separation under vacuum it has to be cared for a sufficient degassing of the suspension prior to the separation, if no antifoam agents shall be used.

After the separation has been completed, the non-dissolved solid matter is dispersed in water, then homogenized and then again subjected to an alkaline extraction. To this end, the temperature is adjusted to a temperature ranging from about 30 to 45° C., particularly to about 40° C., and the pH is adjusted to a value from about 10.5 to 11.5, particularly to about 11.2. Generally, homogenization may take place at each extraction stage. Particularly effective, however, is homogenization by energy input prior to the stage of extraction described here, which may thus be regarded as sufficient to carry out the new method. It is important to add the cleared overflow or the filtrate of the following stage of extraction to the stage of extraction described here so that an enzyme/albumin-ratio from about 1:500 to 1:2,000, particularly of about 1:1250, is present. After an extraction time of about 10 to 60 min., a second separation takes place.

Afterwards, the solid matter is suspended with water for a third time. The pH self-adjusts to between about 10.2 and 10.5, depending of the quality of the water. The temperature is adjusted to between about 25 and 40° C., particularly to about 35° C. To this suspension, in a preferred embodiment, a protease is added. The enzyme/albumin-ratio here ranges from about 1:100 to 1:500, particularly about 1:400. After adding the protease, which also may be a protease mixture, an enzymatic hydrolysis takes place for approximately 3 to 30 min. The hydrolysis times depends of the used amount of enzyme, the respective enzyme activity and the kind of protease. Suitable proteases may be selected from the groups of the serine proteases, the cysteine proteases, the asparagine proteases and/or the metalloproteases.

Some albumin containing substances as raw material for the new method show sensorics that make the resulting albumin isolate inedible, if no further measures are taken. Thus, it has been proved advantageous to add hydrogen peroxide to the second alkaline stage of extraction. The amount of hydrogen peroxide as related to about 35 % hydrogen peroxide solution may range from about 5 to 50 ml per kg albumin, particularly about 20 ml/kg albumin. The concentration has to be adjusted in such a way that damages to the used proteases do not occur.

If the albumin containing starting material contains organic substances that may not be removed by means of an aqueous pre-treatment, it is advantageous to carry out the alkaline extraction in the presence of about 5 to 20% alcohol, particularly of about 10% alcohol. Herein, the solubility of the organic substances is raised so that they remain in the aqueous solution when the albumins are precipitated at the isoelectric point. It is also sufficient to add the alcohol within the second stage of extraction, if it is cared for that the desired alcohol concentration after feeding back the clear overflow of the second separation into the first stage of extraction is not below about 5%.

In the disclosed method, the clear overflow of the first stage of extraction is, in a way which is known as such, adjusted to the product depending isoelectric point of the albumin which is generally in the pH-range of about 4.2 to 4.6 through use of mineral acids or organic acids. At the isoelectric point the albumin is precipitated, and a separation can be carried out with known separation techniques, especially with decanters. The quark-like albumin isolate obtained in this way can be washed and neutralized before drying, to adjust to a desired pH for the end product.

Surprisingly, the step-by-step alkaline extraction using proteases with feeding back the extraction agents results in an albumin quality that is clearly above of the products of known methods. This is the case both with regard to the yield and the sensorics of the method products. At the same time, the process course in the new method can be tuned in such a way, that a water consumption of about 8 l fresh water per kg raw material used is sufficient for all steps of the procedure. Only 25% of this has to be warm water. The arising sewage water is only about 5 l per kg raw material used.

Because of the comparatively high solid matter contents of the processed suspensions, despite the higher pH no greater amounts of acid and/or alkali are used in the new method as compared to classic extraction methods. Instead, a reduction of the amounts of acid and alkali and thus of the resulting salt of up to about 20% may be obtained as compared to commercial methods presently used to prepare albumin isolates.

The albumin isolates obtained by the method according to the invention have a typical high albumin content from about 90 to 94% as related to the dry matter content. Depending of the type of drying applied, the remaining water may be from about 4 to 8%. The yield as related to the albumin content of the starting material is typically from about 80 and 87%. With a tuned process course, the taste of the method products is neutral. A special taste resulting from the starting material can be removed without problems. The protein damages are low. This is documented, for example, by a very low lysinoalanine content of only about 50 to 150 ppm, as related to the albumin in the obtained albumin isolate. Lysinoalanine is an unnatural amino acid derivative formed during processing of foods.

Aspects of the invention can be better understood with reference to the following drawing. While the invention is susceptible to various modifications and alternative forms, specific embodiments thereof are shown by way of example in the drawing and will herein be described in detail. It should be understood, however, that there is no intent to limit the invention to the particular form disclosed, but on the contrary, the invention is to cover all modifications, equivalents, and alternatives falling within the spirit and scope of the invention as defined by the claims.

The flow diagram of the method according to the invention which is shown in the accompanying FIG. 1 indicates the preferred ranges of pH and temperature, and starts with a mash which is prepared by mixing the albumin containing starting material having a small particle size with the clear overflow of a separation step. In the right hand portion of FIG. 1, the three alkaline/enzymatic stages of extraction of the preferred embodiment of the invention are indicated. In the left hand part, the processing of the overflow 1 of the separation 1, i.e., the separation after the first stage of extraction, is shown. At the beginning, this overflow contains the albumin in a dissolved form. Non-dissolved substances within the overflow are removed by clearing. Afterwards, a precipitation of the albumins at the isoelectric point takes place. The precipitate of this precipitation is removed by separation and again suspended in water. By means of a following heat deactivation the enzymes from the extraction of the albumins are inactivated. In the following separation, the overflow is obtained with which the mash is prepared. This overflow does not contain relevant enzyme activity. The downstream neutralization and drying of the solid matter results into the desired albumin isolate.

EXAMPLES

In the following, the embodiments of the invention are further explained and described by way of examples. A protease that may be used to prepare the examples of the invention is protease EC 3.4.21.62, derived from *Bacillus lichenoformis*. Other proteases described previously could be used to achieve the same results. If these proteases do not have the same effective activity at the pH and temperatures applied during the stage of the method according to the exemplary embodiments of the invention as, for example, EC 3.4.21.62, the amount of protease added for producing the same albumin isolates may be increased.

In principle, all proteases disclosed above have at least some effective activity at the pH and temperatures applied during the stages of the examples of the embodiments, and may be used in embodiments of the invention. As noted previously, a low effective protease activity may be compensated for by an increased amount of the protease added.

1. Soya Albumin Isolate

Toasted soya meal is at first processed into an albumin concentrate. The albumin concentrate preferably has a particle size of about 50 µm and is suspended in warm water of approximately 50° C. to a solid matter concentration of the resulting suspension of about 12.5%. This corresponds to the mash in FIG. 1. This suspension is then added with the fed back flow of the downstream second stage of extraction. Afterwards, the pH is adjusted to about 9 with 25% sodium hydroxide. The enzyme/albumin-ratio is about 1:5,500. The suspension is stirred for approximately 15 min at about 45° C. Then, the suspension is separated over a Sedikanter at 6,000×g, with a vacuum of 300 mbar absolute pressure being present in the Sedikanter. The overflow of the Sedikanter contains the already dissolved albumin, the under flow contains the solid matter with the still bonded albumin.

The under flow is again suspended in water so that a solid matter content of 8% is adjusted. The water may be cold.

The suspension obtained in this way is homogenized by means of a pressure drop of 80 bar and added with the cleared overflow of the third stage of extraction. The self-adjusted temperature is about 38° C., and the enzyme/albumin ratio is about 1:1,250. Then, the pH is adjusted again to about 11.2 with 25% sodium hydroxide, and it is stirred for about 15 min. Afterwards, a second separation via a Sedikanter under vacuum takes place. The overflow of this Sedikanter is fed back into the first stage of extraction. The solid matter output, i.e., the under flow is dispersed with cold water and adjusted to a solid matter content of about 6%. The self-adjusting temperature should be below approximately 40° C. Now, proteases having a total activity of 6 Anson Units/kg albumin are added to this suspension, which corresponds to an enzyme/albumin-ratio of about 1:400. This suspension reacts for about 5 min., and is then centrifuged in a Sedikanter in the presence of vacuum in a third separation. The overflow is fed back to the second stage of extraction. The solid matter output or under flow may be neutralized and used as a fiber-containing swelling agent, for example. Within the method described here, however, it is not further used.

The overflow of the first stage of extraction is adjusted to a pH of about 4.3 by means of 15% hydrogen chloride and then centrifuged in a Sedikanter at 300 mbar. The temperature of the input to the Sedikanter is about 45° C. The solid matter output has a dry matter content of about 28%, i.e., the under flow of the Sedikanter contains the albumin, the overflow contains the attendant material and soluble albumin, which is directed to the sewage water. The solid matter is then mixed with water of good quality to about 15% and for a short time heated up to approximately 110° C. By means of this, the solid matter is washed, and the enzymes contained in it are inactivated. After cooling down to about 50° C. a separation of the solid matter from the added water takes place in a standard decanter at about 4,000×g. The overflow of this separation is used for preparing the mash for the first stage of extraction. The under flow is again diluted with water to about 15% dry matter content, neutralized with sodium hydroxide and then spray dried.

2. Potato Albumin Isolate

Albumin containing by-products occurring in the production of starch are at first milled down to a particle size of about 50 μm and then suspended in warm water of a temperature of about 50° C. in such a way that a suspension having a solid matter content of 15% is produced. A protease having an activity of 5 Anson Units/kg protein is added to this suspension. After 5 min. of stirring, the pH is adjusted to about 8.5, and then it is stirred for approximately 10 more minutes. Afterwards, the pH of the suspension is adjusted to about 4.2 by means of hydrogen chloride, and the suspension is centrifuged on a decanter at 4,000×g. The overflow is removed; the solid matter is again suspended in warm water of a temperature of about 50° C., and then processed according to the steps of the exemplary method disclosed in FIG. 1. To this end, the overflow from the second stage of extraction is added to the solid matter suspended in water. The enzyme/albumin-ratio is then approximately 1:6,500. The solid matter content is about 10%. The pH is adjusted to about 9, and the suspension is stirred for about 15 min. At this point, the temperature should be about 45° C. Centrifugation in a Sedikanter at 6,000×g is then performed. Here, the overflow contains the dissolved protein. The under flow, i.e., the solid matter output having a solid matter content of about 26%, is suspended in cold water and added with the overflow of the following third stage of extraction. The temperature self-adjusts to approximately 38° C. The pH is raised to about 11.2 by a 25% sodium hydroxide solution. The enzyme/albumin-ratio is about 1:1,600. This suspension is stirred for about 15 min, with about 20 μl of 25% hydrogen peroxide per kg of solid matter being added after about 10 min. After the stirring time of about 15 min, the suspension is homogenised by via a pressure drop of 80 bars, and then separated in a second Sedikanter under vacuum of 300 mbar. The overflow is added to the first stage of extraction; the under flow containing the solid matter is again suspended in cold water. The temperature of the dispersed solid matter self-adjusts to about 32° C. and the pH reaches approximately 10.5. Proteases having an activity of 4 Anson Units/kg proteins are then added, resulting in an enzyme/albumin-ratio of about 1:500. After about 5 min., this dispersion is centrifuged in a Sedikanter for a third time, again under vacuum of 300 mbar absolute pressure. The overflow of this separation is fed back to the second stage of extraction. The solid matter output, i.e., the under flow, is disposed.

The overflow of the first stage of extraction is adjusted to pH of approximately 4.3 by means of hydrogen chloride. Afterwards, it is centrifuged in a Sedikanter at an under pressure of 300 mbar absolute. The overflow of the Sedikanter is disposed. The quark-like under flow is adjusted with demineralized water to a solid matter content of about 15%. This dispersion is then heated up to about 110° C. for a short time, then cooled down to about 50° C. and centrifuged in a decanter at 4,000×g. The cleared flow or overflow obtained here is used for preparing the mash from the flour of the starting materials for the first stage of extraction. The solid matter output, i.e., the under flow, is neutralized and dried.

Instead of hydrogen peroxide also ethanol can be used in the preparation of potato albumin isolate for extracting undesired organic attendant materials.

It should be emphasized that the above-described embodiments of the disclosed method, particularly, any "preferred" embodiments, are merely possible example implementations. Many variations and modifications may be made to the above-described embodiment(s). All such modifications and variations are intended to be included herein within the scope of this disclosure and protected by the following claims.

Having thus described the invention, at least the following is claimed:

1. A method for preparing an albumin isolate from a substance containing albumin, the method comprising:

grinding the substance to a flour;

suspending the flour in an aqueous solution to form a dispersion;

subjecting the flour in the dispersion to an at least two stage alkaline extraction treatment in the presence of at least one protease to extract the albumin from the flour into the aqueous solution, the protease having an activity in the alkaline extraction treatment, in both of the at least two stages pH-values of the dispersion being approximately 8 to 11.5, and temperatures of the dispersion being from approximately 30 to 60° C.;

in the first stage, the flour being treated with a lower concentration of the at least one protease in relation to a weight of the albumin in the dispersion, with a pH of approximately 8 to 10 and with a temperature of about 30 to 60° C.;

at the end of the first stage, the dispersion being separated into a first overflow containing albumin extracted from the flour, and a fraction of the dispersion containing the remaining flour;

in the second stage, the flour remaining in the fraction of the dispersion being treated with a higher concentration of the at least one protease in relation to the weight of the albumin in the dispersion, with a pH of approximately 10.5 to 11.5 and with a temperature of about 30 to 45° C., provided it is lower than in the first stage; at the end of the second stage, the dispersion being separated into a second overflow containing albumin extracted from the flour, and a sub-fraction of the fraction of the dispersion containing the remaining flour; after separating the dispersion at the end of the second stage, the second overflow being fed back to the first stage of the alkaline extraction treatment of the flour in the dispersion;

after separating the dispersion at the end of the first stage, precipitating the albumin from the first overflow using an acid solution of at least one mineral acid by lowering the pH to isoelectric point of the albumin; and neutralizing the precipitated albumin.

2. The method of claim 1, wherein the albumin containing substance is ground to a flour with an average particle size of 30 to 100 μm.

3. The method of claim 1, wherein the fraction of the dispersion containing the remaining flour is homogenized at the beginning of the second stage of the alkaline extraction treatment of the flour in the dispersion.

4. The method of claim 1, wherein the flour remaining in the sub-fraction of the fraction of the dispersion separated at the end of the second stage is subjected to a third stage of the alkaline extraction treatment in the presence of the at least one protease;

in the third stage
a pH-value of the dispersion being greater than 8, and a temperature of the dispersion being between 30 and 60° C.;
the flour remaining in the fraction of the dispersion being treated with a higher concentration of the at least one protease in relation to the weight of the albumin in the dispersion and with a lower temperature than in the first stage;
at the end of the third stage,
the dispersion being separated into
a third overflow containing albumin extracted from the flour, and
a sub-fraction of the sub-fraction of the fraction of the dispersion containing the remaining flour; and
the third overflow being fed back to the second stage of the alkaline extraction treatment of the flour in the dispersion.

5. The method of claim 4, wherein the at least one protease is added to the solution only in the third stage, and wherein the protease is present in the third overflow fed back to the second stage of the alkaline extraction treatment.

6. The method of claim 1, wherein the at least one protease is selected From the group consisting of serine, cysteine and metalloproteases.

7. The method of claim 1, wherein the at least one protease is inactivated in a suspension containing albumin obtained from the first overflow by means of a heat treatment.

8. The method of claim 1, wherein the albumin is extracted from the flour into the solution, the extraction assisted by at least one substance selected from alcohol and hydrogen peroxide.

9. The method of claim 1, wherein, before subjecting the flour to the at least two stage alkaline extraction treatment in the presence of the at least one protease, the flour is subjected to a pre-treatment using at least one substance selected from the group consisting of lyes, acids and enzymes.

10. The method of claim 1, wherein, at the end of at least one of the stages of the alkaline extraction, the separation of the dispersion into the overflow and the fraction containing the flour is accomplished by a centrifugation of the dispersion in a decanter in which a vacuum is present, wherein the overflow is selected from the first overflow and the second overflow.

11. A method for preparing an albumin isolate from a substance containing albumin, the method comprising:
grinding the substance to a flour;
suspending the flour in an aqueous solution to form a dispersion;
subjecting the flour in the dispersion to a multi-stage alkaline extraction treatment comprising at least two stages in the presence of at least one protease to extract the albumin from the flour into the aqueous solution, the protease having an activity in the alkaline extraction treatment,
in both of the at least two stages
pH-values of the dispersion being from approximately 8 to 11.5, and
temperatures of the dispersion being from approximately 30 to 60° C.;
in the first stage, the flour being treated
with a lower concentration of the at least one protease in relation to a weight of the albumin in the dispersion,
with a pH of approximately 8 to 10 and
with a temperature of about 30 to 60° C.;
at the end of the first stage, the dispersion being separated into
a first overflow containing albumin extracted from the flour, and
a fraction of the dispersion containing the remaining flour;
in the second stage, the flour remaining in the fraction of the dispersion being treated
with a higher concentration of the at least one protease in relation to the weight of the albumin in the dispersion,
with a pH of approximately 10.5 to 11.5 and
with a temperature of about 30 to 45° C., provided it is lower than in the first stage;
at the end of the second stage,
the dispersion being separated into
a second overflow containing albumin extracted from the flour, and
a sub-fraction of the fraction of the dispersion containing the remaining flour;
after separating the dispersion at the end of the second stage, the second overflow being fed back to the first stage of the alkaline extraction treatment of the flour in the dispersion;
after separating the dispersion at the end of the first stage, precipitating the albumin from the first overflow using an acid solution of at least one mineral acid by lowering the pH to isoelectric point of the albumin; and neutralizing the precipitated albumin.

12. The method of claim 11, wherein the albumin containing substance is ground to a flour with an average particle size of 30 to 100 μm.

13. The method of claim 11, wherein the fraction of the dispersion containing the remaining flour is homogenized at the beginning of the second stage of the alkaline extraction treatment of the flour in the dispersion.

14. The method of claim 11, wherein the flour remaining in the sub-fraction of the fraction of the dispersion separated at the end of the second stage is subjected to a third stage of the alkaline extraction treatment in the presence of the at least one protease;

in the third stage
- a pH-value of the dispersion being greater than 8, and a temperature of the dispersion being between 30 and 60° C.;
- the flour remaining in the fraction of the dispersion being treated with a higher concentration of the at least one protease in relation to the weight of the albumin in the dispersion and with a lower temperature than in the first stage;

at the end of the third stage,
- the dispersion being separated into
  - a third overflow containing albumin extracted from the flour, and
  - a sub-fraction of the sub-fraction of the fraction of the dispersion containing the remaining flour; and
- the third overflow being fed back to the second stage of the alkaline extraction treatment of the flour in the dispersion.

15. The method of claim 14, wherein the at least one protease is added to the solution only in the third stage, and wherein the protease is present in the third overflow fed back to the second stage of the alkaline extraction treatment.

16. The method of claim 15, wherein the at least one protease is selected from the group consisting of serine, cysteine, and metalloproteases.

17. The method of claim 11, wherein the at least one protease is inactivated in a suspension containing albumin obtained from the first overflow by means of a heat treatment.

18. The method of claim 11, wherein the albumin is extracted from the flour into the solution, the extraction assisted by at least one substance selected from alcohol and hydrogen peroxide.

19. The method of claim 11, wherein, before subjecting the flour to the at least two stage alkaline extraction treatment in the presence of the at least one protease, the flour is subjected to a pre-treatment using at least one substance selected from the group consisting of lyes, acids and enzymes.

20. The method of claim 11, wherein, at the end of at least one of the stages of the alkaline extraction, the separation of the dispersion into the overflow and the fraction containing the flour is accomplished by a centrifugation of the dispersion in a decanter in which a vacuum is present, wherein the overflow is selected from the first overflow and the second overflow.

21. The method of claim 11, wherein the multi-stage alkaline extraction treatment has two, three, or four stages.

22. The method of claim 11, wherein the mineral acid is chosen from: hydrochloric acid, sulfuric acid, phosphoric acid and combinations thereof.

\* \* \* \* \*